United States Patent [19]

Rideout et al.

[11] 4,136,175

[45] Jan. 23, 1979

[54] PURINE NUCLEOTIDE ANTIVIRAL COMPOSITION AND METHODS OF USE

[75] Inventors: Janet E. Rideout; Richard L. Miller, both of Raleigh; Gertrude B. Elion, Chapel Hill, all of N.C.

[73] Assignee: Burroughs Wellcome Co., Research Triangle Park, N.C.

[21] Appl. No.: 696,519

[22] Filed: Jun. 16, 1976

[30] Foreign Application Priority Data

Jun. 17, 1975 [GB] United Kingdom ............... 25768/75

[51] Int. Cl.² .................. A61K 31/52; C07C 19/20
[52] U.S. Cl. ............................... 424/180; 195/28 N; 195/80 R; 536/27; 536/28
[58] Field of Search .................. 536/26, 27, 28, 29; 424/180

[56] References Cited

U.S. PATENT DOCUMENTS

| 3,300,478 | 1/1967 | Wechter | 536/28 |
|---|---|---|---|
| 3,328,389 | 6/1967 | Shimizu et al. | 536/29 |
| 3,337,530 | 8/1967 | Hanze | 536/28 |
| 3,382,232 | 5/1968 | Honjo et al. | 536/27 |
| 3,448,098 | 6/1969 | Gaines et al. | 536/28 |
| 3,666,856 | 5/1972 | Elion et al. | 536/26 |
| 3,703,507 | 11/1972 | Haskell et al. | 536/27 |

FOREIGN PATENT DOCUMENTS 1386584 3/1975 United Kingdom ............... 536/26

*Primary Examiner*—Johnnie R. Brown
*Attorney, Agent, or Firm*—Donald Brown

[57] ABSTRACT

The nucleotide derivatives of certain 2,6 substituted purines have been discovered to have anti-viral activity. Novel compounds and their pharmaceutically acceptable salts, pharmaceutical formulations containing the compounds of this invention, and the treatment of viral infections with these formulations are all disclosed. 2,6 Diamino-9-($\beta$-D arabinofuranosyl)-purine-5'-phosphate is an example of a more active compound of this invention.

30 Claims, No Drawings

PURINE NUCLEOTIDE ANTIVIRAL COMPOSITION AND METHODS OF USE

This invention relates to purine sugar derivatives which are useful as antiviral agents.

The compounds of this invention are 9-(β-D-arabinofuranosyl) purine -5'-phosphates of the Formula (I)

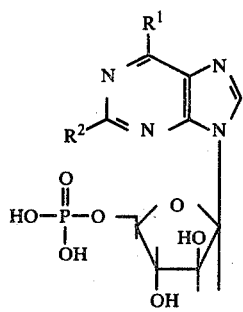

wherein $R^1$ and $R^2$ are the same of different and are each amino or hydroxyl.

The compounds of this invention may also be provided as salts and be used in pharmacological and medical applications as pharmaceutically acceptable salts, although it should be understood that the activity of any salt administered or used medically resides in the nucleotide moiety. In addition, toxic salts can be made and converted to either the acidic nucleotide or pharmaceutically acceptable salts by standard decomposition or exchange methods.

Salts which are especially preferred for therapeutic use are pharmaceutically acceptable salts of the nucleotides of Formula I with organic or inorganic bases containing pharmaceutically acceptable cations such as sodium, potassium, calcium, tetralkylammonium, e.g. tetramethylammonium cations and the like.

The compounds of Formula I and their pharmaceutically acceptable salts are particularly useful in treating viral infections resulting from DNA viruses, of which type vaccinia and herpes are examples.

For viral infections of the eye or other external tissues such as caused by the above viruses the compounds of Formula I or their pharmaceutically acceptable salts would preferably be applied to the infected part of the body of the patient as a solution or topical ointment. The compounds of this invention are also useful in treating systemic vaccinial and herpes viral infections and for such use, the compounds are preferably administered orally or parenterally.

The compounds of this invention are preferably used internally (orally or parenterally) for the treatment of viral infections at dose levels (as nucleotide) of about 1–100 mg/kg of mammal, e.g. mice, man etc., bodyweight, and is preferably used in man in a unit dosage form (administered a few times daily) in the amount of 10 to 250 mg per unit dose depending on the patient being treated. For use as an ointment, or cream the compounds may be presented in a water soluble ointment base, petrolatum, or an oil in water cream base in a concentration of from 0.1 to 10% w/v.

Of the compounds of Formula I, the compound where $R^1$ and $R^2$ are both amino is the most preferred, particularly for its extremely high antiviral activity. This compound, 2,6-diamino-9-(β-D-arabinofuranosyl)-purine-5'-phosphate, is the monophosphate nucleotide of 2,6-diamino-9-(β-D-arabinofuranosyl)purine which has in tests been found to be extremely effective as an antiviral agent, as for example, against the herpes virus. In particular, one hundred percent of mice infected intracerebrally with herpes virus and treated with 2,6-diamino-9-(β-D-arabinofuranosyl)purine, in comparison with five untreated controls, survived at least five days without clinical signs of infection, whereas 60% of the controls died, and the two remaining controls were moribund after five days.

The compound 2,6-diamino-9-(β-D-arabinofuranosyl)purine-5'-phosphate has also shown substantial and unexpectedly high activity against herpes virus.

The nucleotides of this invention have the desirable anti-viral activities of their corresponding nucleosides. These compounds may penetrate cell membranes unchanged or may be hydrolyzed to the corresponding active nucleosides by phosphatases present in mammalian cell membranes. In addition the nucleotides are more soluble in physiologically acceptable solvents and body fluids, making administration of the compounds more convenient and distribution within the body more facile. It is believed that other mammalian enzymes than cell membrane phosphatases may also hydrolyze the nucleotides of this invention in situ to provide the corresponding nucleosides having known activity.

For use as antiviral agents, the purine nucleotides of this invention or their salts may be given parenterally (in an injectable solution), orally (tablets or capsules), used as a suppository, applied as an ophthalmic solution, or applied topically as an ointment, cream, powder, etc., as a pharmaceutical preparation in accordance with known medical or veterinarial practice. The preferred compound is preferably administered at a dosage of about 1 and 100 mg/kg of mammal body weight (i.e. mice, rats, dogs, humans). In a unit dosage the compound is preferably administered at a dosage of about 10–250 mg per unit dose which is preferably given or used a few (2–4) times daily. For external usage the compounds are applied in an ointment or cream in a concentration of 0.1 to 10% w/v.

The compounds of Formula I may be prepared conveniently by the enzymatic or chemical phosphorylation of the corresponding nucleosides of Formula II

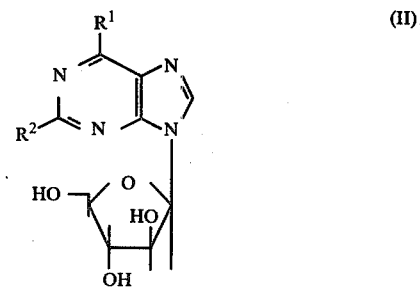

wherein $R^1$ and $R^2$ are as defined above.

Enzymatic phosphorylation of the nucleosides of Formula II may be effected by incubating a reaction mixture containing the nucleoside substrate and a suitable phosphate source with a phosphotransferase enzyme which is capable of phosphorylating in the 5'-position of the sugar moiety. The incubation is generally carried out for about 2 to 36 hours, preferably about 18 to 24 hours, at a temperature of 25° to 45° C., preferably 35° to 40° C., most preferably at about 37° C. Suitable sources of phosphate includes any nucleoside-5'-monophosphate and organic phosphates such as phenyl phosphate and p-nitrophenyl phosphate (generally as the sodium salts). Nucleoside-5'-di- and triphosphates could be used, but mixtures of the mono-, di-, and triphosphates of the substrate nucleosides would result, requiring tedious and expensive purification. The phosphotransferase enzyme preparation is preferably one of bacterial source and may be a preparation of intact cells or a cell-free extract. Suitable bacteria are those which catalyze mainly the phosphorylation at the 5'-position of nucleosides and are found in such genera as Pseudomonas, Alcaligenes, Achromabacter, Flavobacterium, Serratia, and Staphylococcus (such as disclosed in Agr. Biol. Chem. 28, 586–600 (1964)). Particularly convenient are the various strains of *Serratia Marcescens.* Specific purified phosphorylation enzymes may also be used. For example, deoxyguanosine kinase may be used to convert 2-amino-6-hydroxy-9-($\beta$-D-arabinofuranosyl) purine (ara-G) into 2-amino-6-hydroxy-9-($\beta$-D-arabinofuranosyl)purine-5'-phosphate (ara-GMP) or 2-hydroxy-6-amino-9-($\beta$-D-arabinofuranosyl)-purine (ara-iso-G) into 2-hydroxy-6-amino-9-($\beta$-D-arabinofuranosyl)purine-5'-phosphate (ara-iso-GMP). Sources of phosphotransferase other than bacterial may be useful. For example, a useful phosphotransferase preparation may be obtained from carrots.

Chemical phosphorylation is generally complicated by the presence in the nucleoside molecule of several reactive sites in addition to the 5'-hydroxyl moiety. The 2'- and 3'-hydroxyl groups are about as reactive as the 5'-hydroxyl and thus generally must be protected prior to reaction of the nucleoside with a phosphorylating agent and then deblocked later. When blocking groups are used, they may be selectively attached by judicious selection of reactants and reaction conditions, or all three hydroxyls (2', 3' and 5') may be blocked and then the 5'-position selectively deblocked. Alternatively, the 5'-position may be selectively blocked by a bulky blocking group, followed by conventional blocking of the 2'- and 3'-positions and removal of the 5'-bulky blocking group. One example of such a bulky blocking group is the trityl group; 4,4'-dimethoxytrityl chloride has been used for this purpose. Another example is the tert-butyl-dimethylsilyl group.

Phosphorylation at the 5'-position may then be effected and the 2'- and 3'-position deblocked by appropriate means. Generally, substituents on the purine ring may be left unblocked provided the phosphorylation conditions are sufficiently mild not to affect them.

It is not always necessary to block the 2'- and 3'-positions prior to phosphorylation. Derivatives of the phosphoric acid having one to three hydroxy groups replaced by halogen atoms, e.g. chlorine, such as phosphoryl chloride are preferred for phosphorylation. Up to two of the hydroxy groups can also be substituted to form alkyloxy groups carrying for instance further substitutions to form arylalkyloxy groups. Such phosphohalic derivatives or phosphonates are applied under the usual neutral or alkaline conditions, the latter preferably requiring activation, for instance by carbodiimide, e.g. carbodicyclohexylimide, except when it is presented in the form of the anhydride.

Single or substituted alkoxy groups introduced with a phosphonate may be hydrolysed in a suitable aqueous medium in the presence of bases in a subsequent step. Substituted alkoxy groups can also be subjected to hydrogenolysis, preferably in the presence of a catalyst, according to the usual techniques of cleaving, for instance benzyl grouping, in this manner.

A preferred method of phosphorylating the nucleosides of this invention involves reaction of the unprotected nucleosides with phosphoryl chloride ($POCl_3$) in the presence of trialkylphosphate and preferably in the presence of a small amount of water at a temperature of about 0° C. or less. With these reaction conditions phosphorylation generally is preferentially accomplished on the 5'-position. Apparently, the 5'-phosphorodichloridate is formed initially and is readily hydrolyzed to the corresponding phosphate upon treatment with water at a slightly basic pH.

Other useful methods for preparing the 5'-monophosphates of this invention include reaction of the unprotected nucleoside with phosphoryl chloride in dry pyridine. This procedure generally gives a mixture of the 2'-, 3'- and 5'-phosphates in which the 5'-phosphate predominates. Separation and purification of the 5'-phosphate may be effected by standard chromatographic procedures. Reaction of the unprotected nucleoside with $\beta,\beta,\beta$-trichloro ethylchlorophosphonate at low temperatures followed by removal of the trichloroethyl blocking groups from the 5'-position on the sugar moiety by the action of zinc dust in aqueous pyridine also yields the corresponding 5'-nucleotide.

The nucleotides of this invention may also be made by enzymatic conversion of the purine substituents at positions 2 and 6. Enzymes are known which provide an interconversion of a hydroxy and an amino group in the 2nd position, respectively, and also the conversion of an amino group into a hydroxy group in the 6th position. For example, ara-GMP (I, $R^1$=OH, $R^2$=$NH_2$) may be made by enzymatic conversion from ara-DAPMP (I, $R^1$=$R^2$=$NH_2$) by the action of adenylate deaminase or from ara-XMP (I, $R^1$=$R^2$=OH) by the action of GMP synthetase.

Thus the present invention provides the above methods of preparation of the compound of Formula I and the preferred compound wherein $R^1$ and $R^2$=$NH_2$ and addition salts thereof.

This invention also provides pharmaceutical compositions or preparations comprising a compound of Formula I or a pharmaceutically acceptable salt thereof and a pharmaceutically acceptable carrier thereof. The compositions may be used orally, parenterally, or topically depending on whether the preparation is used to treat internal or external viral infections caused by DNA viruses.

This invention also provides a method for treating viral infections caused by DNA viruses in mammals, (i.e. mice, rats, dogs, man, etc.) by administering an effective non-toxic antiviral amount of a compound of Formula I (preferably were $R^1$=$R^2$=$NH_2$) or a salt thereof to the infected mammal. DNA viruses are those viruses which utilize DNA as building blocks.

The invention also provides novel and useful compounds of the above formulae.

For oral administration, fine powders or granules of the compounds may contain diluting, dispersing and/or surface active agents, and may be presented in a draft, in water or in a syrup, in capsules or cachets in the dry state or in a non-aqueous suspension where in suspending agents may be included; in tablets, when binders and lubricants may be included; or in a suspension in water or a syrup.

Where desirable or necessary flavoring, preserving, suspending, thickening or emulsifying agents can be included. Tablets and granules are preferred, and these may be coated. For parenteral administration, the compounds may be presented in aqueous injection solutions which may contain antioxidants, buffers, etc.

EXAMPLE 1.
2,6-Diamino-9-($\beta$-D-arabinofuranosyl)purine-5'-phosphate (Ara-DAPMP; I, $R^1=R^2=NH_2$)

A suspension of dry 2,6-diamino-9-($\beta$-D-arabinofuranosyl)purine (0.57 g) in triethyl phosphate (3.5 ml) was cooled with stirring to $-15°$ C. Phosphorus oxychloride (0.75 ml) was then added. After one hour of stirring at $-15°$ C., additional triethyl phosphate (2 ml) was added, and 30 minutes later additional phosphorus oxychloride (0.28 ml) was added. The cooling bath was allowed to warm up to $-2°$ C. over the next hour, and the reaction mixture maintained at that temperature for an addition 2.5 hours. The reaction mixture was filtered, removing unreacted nucleosides (0.134 g). The filtrate was poured onto a mixture of water and ice and the pH of the mixture adjusted to 7.8 by the addition of 1 N sodium hydroxide. The solution was extracted twice with chloroform. The aqueous layer was diluted to a total volume of six liters and the nucleotides adsorbed onto Dowex 1-x8 (chloride) (12 g). The resin was washed with water, and the nucleotide was eluted with 1 M lithium chloride, pH 6.5. The eluate was lyophilized. The lithium chloride in the lyophilized powder was extracted wit acetone/methanol (9:1). The residue was dissolved in water, filtered and the nucleotide adsorbed into activated charcoal. The ara-DAPMP was eluted from the charcoal with 10% ammonia/50% ethanol. The volume of the eluant was decreased by about 60–70% under reduced pressure at 40° C. and then lyophilized to give pure 2,6-diamino-9-($\beta$-D-arabinofuranosyl)purine-5'-phosphate (44 mg) as a white powder, m.p. > 300° C. (darkens at 190° C.). It was shown to be >99% pure by high pressure liquid chromotography. Its U.V. spectra in 0.1 N HCl: $\lambda$max at 252 and 289 nm and $\lambda$min at 233 and 270 nm; in 0.1 N NaOH: $\lambda$max at 254 and 278 nm and $\lambda$min at 236 and 265 nm.

EXAMPLE 2.
2-Amino-6-hydroxy-9-($\beta$-D-arabinofuranosyl)purine-5'-phosphate (Ara-GMP); I, $R^1=OH$, $R^2=NH_2$)

A reaction mixture containing Tris-succinate (100 mM, pH 5.9), potassium chloride (100 mM), $\beta$-mercaptoethanol (5 mM), 2,6-diamino-9-($\beta$-D-arabinofuranosyl)purine-5'-phosphate (8.6 mM), and AMP deaminase (55 units) in sufficient water to give a total volume of 10 ml was allowed to stand at 25° C. for 24 hours. The reaction mixture was then filtered and the filtrate diluted to 100 ml. The nucleotides were adsorbed onto activated charcoal and subsequently eluted with aqueous pyridine (10%, 25 ml). The eluant was evaporated to dryness at 30° C. under reduced pressure. The resulting powder was dissolved in water (25 ml), filtered and lyophilized to give 2-amino-6-hydroxy-9-($\beta$-D-arabinofuranosyl)purine-5'-phosphate (30 mg). This product was shown to be >99% pure by high pressure liquid chromatography; its U.V. spectra in 0.1 N HCl showed $\lambda$max at 255 and 276(sh) nm and $\lambda$min at 219 nm and in 0.1 N NaOH $\lambda$max at 258 nm and $\lambda$min at 231 nm. Treatment of the product with 5'-nucleotidase gave 2-amino-6-hydroxy-9-($\beta$-D-arabinofuransoyl)purine which was identical with an authentic sample.

EXAMPLE 3.
2-Hydroxy-6-amino-9-($\beta$-D-arabinofuranosyl)purine-5'-phosphate (Ara-iso-GMP; I, $R^1=NH_2$, $R^2=OH$)

A partially purified phosphotransferase preparation from *Serratia marcescens* was used to synthesize ara-iso-GMP from ara-iso-G. *S. marcescens* ATCC 14227 was grown in Difco Nutrient Broth medium to early stationary phase and harvested by centrifugation. The cells were broken in a French press at 20,000 psi and the resulting suspension centrifuged at 5000 × g for 15 minutes to remove cell debris. After treating the supernatant with ribonuclease and deoxyribonuclease, the suspension was centrifuged at 100,000 × g for two hours. The supernatant was concentrated using an Amicon Ultrafiltration Membrane which retained molecules of molecular weight greater than 100,000. Virtually all of the enzyme was retained by the membrane. Relative to the crude extract, an overall enzyme yield of 50% ad a 4-fold purification was obtained.

A reaction mixture having a total volume of 2 ml and containing 300 mM sodium acetate buffer, pH 4.0, 1 mM cupric sulfate, 220 mM p-nitrophenyl phosphate, 16 mM 2-hydroxy-6-amino-9-($\beta$-D-arabinofuranosyl)purine (ara-iso-G), and a portion of the above enzyme preparation containing 10 mg of protein was incubated at 37° C. for 3 days, centrifuged, and the supernatant lyophilized.

The lyophilized powder was dissolved in water and applied to a water-equilibrated Bio-Rad P-2 polyacrylamide gel column (1 × 60 cm). The nucleotide fractions, eluted with water, were pooled, lyophilized and applied to a cellulose preparative thin layer plate (Uniplate Avicel F, 1000$\mu$ thick). The plate was developed in n-propanol/water: 7/3. Bands corresponding to the nucleotide were eluted from the cellulose with water and lyophilized. The lyophilized powder was dissolved in water and applied to a water-equilibrated Sephadex G-10 column (0.9 33 100 cm) and eluted with water. The fraction containing nucleotide were pooled and lyophilized to give 2-hydroxy-6-amino-9-($\beta$-D-arabinofuranosyl)purine-5'-phosphate (2 mg) as a white powder. The product was shown to be >99% pure by high pressure liquid chromatography; it showed a single spot on cellulose thin layer chromatography; its U.V. spectra were the same as those of isoguanine arabinoside (in 0.1 N HCl $\lambda$max 235(sh), 282 nm; $\lambda$min 248 nm; pH 7 $\lambda$max 247, 288 nm; $\lambda$min 232, 263 nm; 0.1 NaOH $\lambda$max 250, 281, 320(sh) nm; $\lambda$min 237, 262 nm); its base to phosphate ratio was 1:1.1; and treatment with 5'-nucleotidase cleaved it to isoguanine arabinoside.

EXAMPLE 4.
2,6-Dihydroxy-9-($\beta$-D-arabinofuranosyl)purine-5'-phosphate (Ara-XMP; I, $R^1=R^2=OH$)

A reaction mixture (20 ml) containing 25 mM Tris-Cl, pH 8.0, 100 mM potassium chloride, 0.4 mM NAD+, 15 mM pyruvic acid, 10 mM 6-hydroxy-9-($\beta$-D-arabinofuranosyl)purine-5'-phosphate (ara-IMP), 15 ng lactate dehydrogenase and 35 milliunits of IMP dehydrogenase was incubated at 30° C. for 24 hrs. An additional 25 milliunits of IMP dehydrogenase were added and incubation was continued another 48 hrs. A final 25 milliunits of IMP dehydrogenase were added and incubation continued another 24 hrs. (96 hrs total). The reaction mixture was filtered and lyophilized. The lyophilized powder was dissolved in a minimum amount of water and applied to a water-equilibrated Bio-Rad P-2 polyacrylamide gel column (2.5 × 90 cm). The column was eluted with water, and the fractions containing U.V. absorbing material were pooled, applied to a DEAE A-25 Sephadex column and chromatographed according to the method of Caldwell [J. Chromatography, 44, 331 (1969)] using a pH 4.7 triethylammonium acetate buffer. Fractions containing ara-XMP were pooled, lyophilized and reapplied to the water-equilibrated Bio-Rad P-2 polyacrylamide gel column. The column was eluted with water and the fractions containing ara-XMP were pooled and lyophilized to give 2,6-dihydroxy-9-(β-D-arabinofuranosyl)purine-5'-phosphate (1.2 mg) as a white powder. The product was shown to be >92% pure by high pressure liquid chromatography; its U.V. spectrum in 0.1 N NaOH λmax 248, 276 nm; it was converted by XMP aminase to a product identical with an authentic sample of ara-GMP; it was cleaved by 5'-nucleotidase to ara-X [2,6-dihydroxy-9-(β-D-arabinofuranosyl)purine].

EXAMPLE 5. Sodium 2,6-Diamino-9-(β-D-arabinofuranosyl)purine-5'-phosphate (Sodium Salt of I, $R^1=R^2=NH_2$)

2,6-Diamino-9-(β-D-arabinofuranosyl)purine-5'-phosphate (I, $R^1=R^2=NH_2$) (1 mM) is dissolved in 0.1 N sodium hydroxide (10 ml) and then lyophylized to give the mono sodium salt of 2,6-diamino-9-(β-D-arabinofuranosyl)purine-5'-phosphate in virtually quantitative yield.

We claim:
1. A pharmaceutical composition which comprises a DNA antiviral effective amount of a compound of formula (I) or a pharmaceutically acceptable salt thereof,

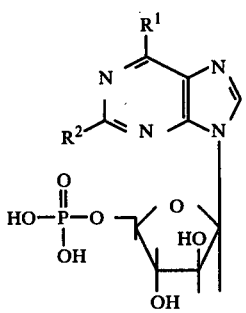

(I)

wherein $R^1$ and $R^2$ are amino together with a pharmaceutically acceptable carrier therefor.

2. A pharmaceutical composition as claimed in claim 1 which is in the form of a tablet or capsule.
3. A pharmaceutical composition as claimed in claim 1 which is in the form of an ointment or cream.
4. A pharmaceutical composition in unit dose form for oral or parenteral administration as claimed in claim 1 comprising the compound of formula (I) in an amount of 10 to 250 mg per unit dose.
5. A pharmaceutical composition for external administration as claimed in claim 1, comprising the compound of formula (I) in an amount of 0.1 to 10% w/v.
6. A method of treating DNA viral infections in mammals, comprising the administration of an effective non-toxic DNA antiviral amount of a compound of formula (I)

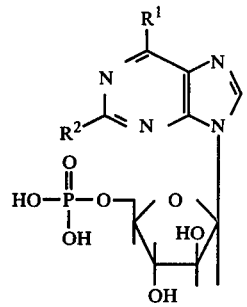

or a pharmaceutically acceptable salt thereof.

7. A method as claimed in claim 6 wherein administration is by topical application.
8. A method as claimed in claim 6 wherein administration is by the oral route.
9. A method as claimed in claim 6 wherein administration is by the parenteral route.
10. A method as claimed in claim 6, wherein the compound of formula (I) is administered in a dose of from 1 to 100 mg/kg body weight.
11. A method as claimed in claim 10 wherein the dose is repeated at least twice daily.
12. A pharmaceutical composition which comprises a DNA antiviral effective amount of a compound of formula (I) or a pharmaceutically acceptable salt thereof (I)

wherein $R^1$ is amino and $R^2$ is hydroxyl together with a pharmaceutically acceptable carrier therefor.

13. The composition of claim 12 in unit dose form.
14. The composition of claim 13 in which the amount of the compound is 10 to 250 mg.
15. The composition of claim 12 as a cream or ointment.
16. The composition of claim 15 in which the concentration of the compound is 0.1 to 10% w/v.
17. The method of claim 6 in which $R^1$ and $R^2$ is amino.
18. The method of claim 6 in which $R^1$ and $R^2$ is hydroxyl.
19. The method of claim 6 in which $R^1$ is amino and $R^2$ is hydroxyl.
20. The method of claim 6 in which $R^1$ is hydroxyl and $R^2$ is amino.
21. The method of claim 6 in which the compound is 2,6-diamino-9-(β-D-arabinofuranosyl)-purine-5'-phosphate.
22. The method of claim 6 in which the compound is a pharmaceutically acceptable salt of 2,6-diamino-9-(β-D-arabinofuranosyl)-purine-5'-phosphate.
23. The method of claim 21 in which the amount is 1 to 100 mg/kg.

24. The method of claim 22 in which the amount is 1 to 100 mg/kg based on the anion portion of the salt.

25. The method of claim 19 in which the amount is 1 to 100 mg/kg of the nucleotide.

26. The method of claim 6 in which virus infection is caused by herpes or vaccinia.

27. The method of claim 16 in which the virus infection is caused by herpes or vaccinia.

28. The method of claim 19 in which the virus infection is caused by herpes or vaccinia.

29. A pharmaceutical composition which comprises a DNA antiviral effective amount of a compound of formula (I) or a pharmaceutically acceptable salt thereof

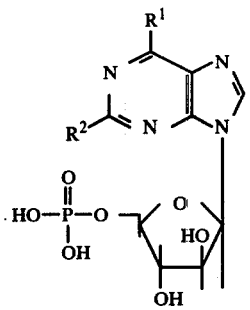

wherein $R^1$ is hydroxyl and $R^2$ is amino together with a pharmaceutically acceptable salt thereof, said composition in unit dose form.

30. A pharmaceutical composition which comprises a DNA antiviral effective amount of a compound of formula (I) or a pharmaceutically acceptable salt thereof

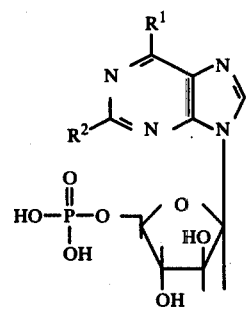

wherein $R^1$ is hydroxyl and $R^2$ is amino together with a pharmaceutically acceptable salt thereof, said composition as an ointment or cream.

* * * * *